(12) United States Patent
Merlo et al.

(10) Patent No.: US 12,336,923 B2
(45) Date of Patent: *Jun. 24, 2025

(54) SCAFFOLD LOADING AND DELIVERY SYSTEMS

(71) Applicant: Lyra Therapeutics, Inc., Watertown, MA (US)

(72) Inventors: Jon Merlo, Boston, MA (US); Lee Core, Needham, MA (US); Garrett Prahl, Brooklyn Park, MN (US); Travis White, Rockford, MN (US); Bryan Goh, Minneapolis, MN (US); Randy Beyreis, Cocoran, MN (US)

(73) Assignee: LYRA THERAPEUTICS, INC., Watertown, MA (US)

( * ) Notice: Subject to any disclaimer, the term of this patent is extended or adjusted under 35 U.S.C. 154(b) by 1107 days.

This patent is subject to a terminal disclaimer.

(21) Appl. No.: 17/192,310

(22) Filed: Mar. 4, 2021

(65) Prior Publication Data

US 2021/0186728 A1 Jun. 24, 2021

Related U.S. Application Data

(63) Continuation of application No. 15/376,842, filed on Dec. 13, 2016, now Pat. No. 10,973,664.

(60) Provisional application No. 62/273,188, filed on Dec. 30, 2015.

(51) Int. Cl.
*A61F 2/95* (2013.01)
*A61F 2/966* (2013.01)

(52) U.S. Cl.
CPC .......... *A61F 2/9525* (2020.05); *A61F 2/9522* (2020.05); *A61F 2/966* (2013.01); *A61F 2/9517* (2020.05); *A61F 2002/9665* (2013.01)

(58) Field of Classification Search
CPC ...... A61F 2/966; A61F 2/9522; A61F 2/9525; A61F 2002/9665
See application file for complete search history.

(56) References Cited

U.S. PATENT DOCUMENTS

| | | |
|---|---|---|
| 4,886,062 A | 12/1989 | Wiktor |
| 5,133,732 A | 7/1992 | Wiktor |
| 5,170,802 A | 12/1992 | Mehra |
| 5,224,491 A | 7/1993 | Mehra |
| 5,265,601 A | 11/1993 | Mehra |
| 5,336,163 A | 8/1994 | DeMane et al. |
| 5,591,198 A | 1/1997 | Bovie et al. |
| 5,613,981 A | 3/1997 | Boyle et al. |
| 5,653,727 A | 8/1997 | Wiktor |
| 5,897,521 A | 4/1999 | Lavigne |
| 5,899,934 A | 5/1999 | Amundson et al. |
| 5,913,896 A | 6/1999 | Bovie et al. |
| 6,047,431 A | 4/2000 | Canonica |
| 6,161,029 A | 12/2000 | Spreigl et al. |
| 6,301,507 B1 | 10/2001 | Bakels et al. |
| 6,330,481 B1 | 12/2001 | Van Wiik et al. |
| 6,346,116 B1 | 2/2002 | Brooks et al. |
| 6,385,491 B1 | 5/2002 | Lindemans et al. |
| 6,449,507 B1 | 9/2002 | Hill et al. |
| 6,487,446 B1 | 11/2002 | Hill et al. |
| 6,532,388 B1 | 3/2003 | Hill et al. |

(Continued)

*Primary Examiner* — William H Matthews
(74) *Attorney, Agent, or Firm* — Medlen & Carroll, LLP

(57) ABSTRACT

This disclosure pertains, inter alia, to scaffold loading and delivery devices, assemblies, systems and methods of using the same.

9 Claims, 7 Drawing Sheets

(56) References Cited

U.S. PATENT DOCUMENTS

| | | | |
|---|---|---|---|
| 6,543,452 B1 | 4/2003 | Lavigne | |
| 6,628,987 B1 | 9/2003 | Hill et al. | |
| 6,718,208 B2 | 4/2004 | Hill et al. | |
| 6,770,080 B2 | 8/2004 | Kaplan et al. | |
| 6,863,684 B2 | 3/2005 | Kim et al. | |
| 6,904,318 B2 | 6/2005 | Hill et al. | |
| 6,909,920 B2 | 6/2005 | Lokhoff et al. | |
| 6,923,828 B1 | 8/2005 | Wiktor | |
| 6,945,992 B2 | 9/2005 | Goodson, IV et al. | |
| 7,184,828 B2 | 2/2007 | Hill et al. | |
| 7,184,829 B2 | 2/2007 | Hill et al. | |
| 7,323,008 B2 | 1/2008 | Kantor et al. | |
| 7,356,903 B2 | 4/2008 | Krivoruchko et al. | |
| 7,361,168 B2 | 4/2008 | Makower et al. | |
| 7,386,351 B2 | 6/2008 | Hine et al. | |
| 7,410,480 B2 | 8/2008 | Muni et al. | |
| 7,419,497 B2 | 9/2008 | Muni et al. | |
| 7,462,175 B2 | 12/2008 | Chang et al. | |
| 7,500,971 B2 | 3/2009 | Chang et al. | |
| 7,520,876 B2 | 4/2009 | Ressemann et al. | |
| 7,544,192 B2 | 6/2009 | Eaton et al. | |
| 7,547,323 B2 | 6/2009 | Lavigne | |
| 7,559,925 B2 | 7/2009 | Goldfarb et al. | |
| 7,578,899 B2 | 8/2009 | Edwin et al. | |
| 7,615,072 B2 | 11/2009 | Rust et al. | |
| 7,641,644 B2 | 1/2010 | Chang et al. | |
| 7,645,272 B2 | 1/2010 | Chang et al. | |
| 7,648,367 B1 | 1/2010 | Makower et al. | |
| 7,654,997 B2 | 2/2010 | Makower et al. | |
| 7,662,141 B2 | 2/2010 | Eaton et al. | |
| 7,662,142 B2 | 2/2010 | Eaton et al. | |
| 7,678,099 B2 | 3/2010 | Ressemann et al. | |
| 7,686,798 B2 | 3/2010 | Eaton et al. | |
| 7,691,094 B2 | 4/2010 | Eaton et al. | |
| 7,697,972 B2 | 4/2010 | Verard et al. | |
| 7,704,259 B2 | 4/2010 | Kaplan et al. | |
| 7,713,255 B2 | 5/2010 | Eaton et al. | |
| 7,717,933 B2 | 5/2010 | Becker | |
| 7,717,955 B2 | 5/2010 | Lane et al. | |
| 7,720,521 B2 | 5/2010 | Chang et al. | |
| 7,727,186 B2 | 6/2010 | Makower et al. | |
| 7,727,226 B2 | 6/2010 | Chang et al. | |
| 7,740,642 B2 | 6/2010 | Becker | |
| 7,753,929 B2 | 7/2010 | Becker | |
| 7,753,930 B2 | 7/2010 | Becker | |
| 7,771,409 B2 | 8/2010 | Chang et al. | |
| 7,803,150 B2 | 9/2010 | Chang et al. | |
| 7,806,919 B2 | 10/2010 | Bloom et al. | |
| 7,815,673 B2 | 10/2010 | Bloom et al. | |
| 7,842,062 B2 | 11/2010 | Keith et al. | |
| 7,854,744 B2 | 12/2010 | Becker | |
| 7,951,131 B2 | 1/2011 | Eaton et al. | |
| 7,879,061 B2 | 2/2011 | Keith et al. | |
| 7,914,639 B2 | 3/2011 | Layne et al. | |
| 7,951,130 B2 | 3/2011 | Eaton et al. | |
| 7,918,871 B2 | 4/2011 | Truitt et al. | |
| 7,951,132 B2 | 5/2011 | Eaton et al. | |
| 7,951,133 B2 | 5/2011 | Eaton et al. | |
| 7,951,134 B2 | 5/2011 | Eaton et al. | |
| 7,951,135 B2 | 5/2011 | Eaton et al. | |
| 7,955,346 B2 | 6/2011 | Mauch et al. | |
| 7,967,807 B2 | 6/2011 | Murray | |
| 7,967,857 B2 | 6/2011 | Lane | |
| 7,972,378 B2 | 7/2011 | Tabor et al. | |
| 7,993,350 B2 | 8/2011 | Ventura et al. | |
| 7,993,675 B2 | 8/2011 | Oliver et al. | |
| 8,025,635 B2 | 9/2011 | Eaton et al. | |
| 8,034,099 B2 | 10/2011 | Pellegrini | |
| 8,046,052 B2 | 10/2011 | Verard et al. | |
| 8,052,693 B2 | 11/2011 | Shahoian | |
| 8,052,750 B2 | 11/2011 | Tuval et al. | |
| 8,088,101 B2 | 1/2012 | Chang et al. | |
| 8,100,933 B2 | 1/2012 | Becker | |
| 8,109,918 B2 | 2/2012 | Eaton et al. | |
| 8,114,062 B2 | 2/2012 | Muni et al. | |
| 8,114,113 B2 | 2/2012 | Becker | |
| 8,118,757 B2 | 2/2012 | Morriss | |
| 8,123,722 B2 | 2/2012 | Chang et al. | |
| 8,126,549 B2 | 2/2012 | Sigg et al. | |
| 8,142,422 B2 | 3/2012 | Makower et al. | |
| 8,146,400 B2 | 4/2012 | Goldfarb et al. | |
| 8,152,842 B2 | 4/2012 | Schlun | |
| 8,157,940 B2 | 4/2012 | Edwin et al. | |
| 8,172,828 B2 | 5/2012 | Chang et al. | |
| 8,182,432 B2 | 5/2012 | Kim et al. | |
| 8,190,389 B2 | 5/2012 | Kim et al. | |
| 8,192,420 B2 | 6/2012 | Morriss et al. | |
| 8,206,349 B2 | 6/2012 | Slenker et al. | |
| 8,211,169 B2 | 7/2012 | Lane et al. | |
| 8,241,266 B2 | 8/2012 | Keith et al. | |
| 8,249,700 B2 | 8/2012 | Clifford et al. | |
| 8,273,253 B2 | 9/2012 | Curran | |
| 8,277,503 B2 | 10/2012 | Lavigne | |
| 8,277,504 B2 | 10/2012 | Lavigne | |
| 8,282,667 B2 | 10/2012 | Drontle et al. | |
| 8,313,762 B2 | 11/2012 | Oliver et al. | |
| 8,317,816 B2 | 11/2012 | Becker | |
| 8,328,865 B2 | 12/2012 | Bales, Jr. et al. | |
| 8,328,867 B2 | 12/2012 | Dolan et al. | |
| 8,333,799 B2 | 12/2012 | Bales, Jr. et al. | |
| 8,333,800 B2 | 12/2012 | Bruszewski et al. | |
| 8,337,454 B2 | 12/2012 | Eaton et al. | |
| 8,337,650 B2 | 12/2012 | Edwin et al. | |
| 8,348,969 B2 | 1/2013 | Keith et al. | |
| 8,348,995 B2 | 1/2013 | Tuval et al. | |
| 8,348,996 B2 | 1/2013 | Tuval et al. | |
| 8,353,952 B2 | 1/2013 | Thompson et al. | |
| 8,377,083 B2 | 2/2013 | Mauch et al. | |
| 8,414,473 B2 | 4/2013 | Jenkins et al. | |
| 8,414,643 B2 | 4/2013 | Tuval et al. | |
| 8,425,457 B2 | 4/2013 | John et al. | |
| 8,425,488 B2 | 4/2013 | Clifford et al. | |
| 8,435,261 B2 | 5/2013 | Arcand et al. | |
| 8,435,290 B2 | 5/2013 | Clifford et al. | |
| 8,439,687 B1 | 5/2013 | Morriss et al. | |
| 8,452,392 B2 | 5/2013 | Morriss et al. | |
| 8,460,323 B2 | 6/2013 | Mauch et al. | |
| 8,468,667 B2 * | 6/2013 | Straubinger | A61F 2/2427 29/280 |
| 8,485,199 B2 | 7/2013 | Morriss | |
| 8,500,793 B2 | 8/2013 | Zipse et al. | |
| 8,500,801 B2 | 8/2013 | Eberhardt et al. | |
| 8,529,548 B2 | 9/2013 | Blott et al. | |
| 8,529,941 B2 | 9/2013 | Hakimimehr et al. | |
| 8,535,707 B2 | 9/2013 | Arensdorf et al. | |
| 8,540,694 B2 | 9/2013 | Flaherty et al. | |
| 8,551,156 B2 | 10/2013 | Wack et al. | |
| 8,562,672 B2 | 10/2013 | Bonhoeffer et al. | |
| 8,563,510 B2 | 10/2013 | Hakimimehr et al. | |
| 8,568,439 B2 | 10/2013 | Keith et al. | |
| 8,585,728 B2 | 11/2013 | Keith et al. | |
| 8,585,729 B2 | 11/2013 | Keith et al. | |
| 8,585,730 B2 | 11/2013 | Eaton et al. | |
| 8,585,731 B2 | 11/2013 | Abbate et al. | |
| 8,617,337 B2 | 12/2013 | Layne et al. | |
| 8,623,043 B1 | 1/2014 | Keith et al. | |
| 8,647,379 B2 | 2/2014 | McDermott et al. | |
| 8,647,458 B2 | 2/2014 | Banas et al. | |
| 8,657,846 B2 | 2/2014 | Keith et al. | |
| 8,657,867 B2 | 2/2014 | Dorn et al. | |
| 8,663,192 B2 | 3/2014 | Hester et al. | |
| 8,673,000 B2 | 3/2014 | Tabor et al. | |
| 8,673,099 B2 | 3/2014 | Bogert | |
| 8,691,288 B2 | 4/2014 | Myntti | |
| 8,702,626 B1 | 4/2014 | Kim et al. | |
| 8,702,702 B1 | 4/2014 | Edwards et al. | |
| 8,715,169 B2 | 5/2014 | Chang et al. | |
| 8,721,591 B2 | 5/2014 | Chang et al. | |
| 8,740,839 B2 | 6/2014 | Eaton et al. | |
| 8,740,929 B2 | 6/2014 | Gopferich et al. | |
| 8,747,297 B2 | 6/2014 | Miyoshi et al. | |
| 8,747,389 B2 | 6/2014 | Goldfarb et al. | |
| 8,747,460 B2 | 6/2014 | Tuval et al. | |
| 8,758,420 B2 | 6/2014 | Dorn et al. | |

(56) References Cited

U.S. PATENT DOCUMENTS

| | | |
|---|---|---|
| 8,763,222 B2 | 7/2014 | Abbate et al. |
| 8,764,709 B2 | 7/2014 | Chang et al. |
| 8,764,726 B2 | 7/2014 | Chang et al. |
| 8,764,729 B2 | 7/2014 | Muni et al. |
| 8,764,786 B2 | 7/2014 | Becker |
| 8,765,715 B2 | 7/2014 | Oliver et al. |
| 8,777,017 B2 | 7/2014 | Curran |
| 8,777,911 B2 | 7/2014 | Heagle et al. |
| 8,777,926 B2 | 7/2014 | Chang et al. |
| 8,795,713 B2 | 8/2014 | Makower et al. |
| 8,801,670 B2 | 8/2014 | Drontle et al. |
| 8,801,775 B2 | 8/2014 | Griswold |
| 8,801,776 B2 | 8/2014 | House et al. |
| 8,802,131 B2 | 8/2014 | Arensdorf et al. |
| 8,828,041 B2 | 9/2014 | Chang et al. |
| 8,834,513 B2 | 9/2014 | Hanson et al. |
| 8,834,564 B2 | 9/2014 | Tuval et al. |
| 8,840,602 B2 | 9/2014 | Morris et al. |
| 8,845,619 B2 | 9/2014 | Blott et al. |
| 8,852,143 B2 | 10/2014 | Chang et al. |
| 8,858,586 B2 | 10/2014 | Chang et al. |
| 8,858,974 B2 | 10/2014 | Eaton et al. |
| 8,864,774 B2 | 10/2014 | Liu et al. |
| 8,864,787 B2 | 10/2014 | Muni et al. |
| 8,870,893 B2 | 10/2014 | Makower et al. |
| 8,876,894 B2 | 11/2014 | Tuval et al. |
| 8,876,895 B2 | 11/2014 | Tuval et al. |
| 8,888,686 B2 | 11/2014 | Drontle et al. |
| 8,894,614 B2 | 11/2014 | Muni et al. |
| 8,905,922 B2 | 12/2014 | Makower et al. |
| 8,920,419 B2 | 12/2014 | Edwards et al. |
| 8,926,689 B2 | 1/2015 | Bogert |
| 8,932,276 B1 | 1/2015 | Morriss et al. |
| 8,945,088 B2 | 2/2015 | Chang et al. |
| 8,951,225 B2 | 2/2015 | Evard et al. |
| 8,968,269 B2 | 3/2015 | Becker |
| 8,979,888 B2 | 3/2015 | Morriss et al. |
| 8,986,341 B2 | 3/2015 | Abbate et al. |
| 8,997,998 B2 | 4/2015 | Curran et al. |
| 9,005,284 B2 | 4/2015 | Ressemann |
| 9,011,363 B2 | 4/2015 | Clopp et al. |
| 9,192,692 B2 | 4/2015 | Medina et al. |
| 9,022,967 B2 | 5/2015 | Oliver et al. |
| 9,039,657 B2 | 5/2015 | Makower et al. |
| 9,039,680 B2 | 5/2015 | Makower et al. |
| 9,050,440 B2 | 6/2015 | Becker |
| 9,055,965 B2 | 6/2015 | Chang et al. |
| 9,072,619 B2 | 7/2015 | Lam et al. |
| 9,072,681 B2 | 7/2015 | Hakimimehr et al. |
| 9,078,783 B2 | 7/2015 | Morriss et al. |
| 9,084,691 B2 | 7/2015 | Wack et al. |
| 9,084,876 B2 | 7/2015 | Makower et al. |
| 9,089,258 B2 | 7/2015 | Goldfarb et al. |
| 9,095,364 B2 | 8/2015 | Muni et al. |
| 9,095,646 B2 | 8/2015 | Chow et al. |
| 9,101,384 B2 | 8/2015 | Makower et al. |
| 9,101,739 B2 | 8/2015 | Lesch, Jr. et al. |
| 9,114,040 B2 | 8/2015 | Dorn et al. |
| 9,138,569 B2 | 9/2015 | Edgren et al. |
| 9,144,663 B2 | 9/2015 | Ahlberg et al. |
| 9,192,751 B2 | 11/2015 | Macaulay et al. |
| 9,220,879 B2 | 12/2015 | Chang et al. |
| 9,238,125 B2 | 1/2016 | Vaccaro et al. |
| 9,241,834 B2 | 1/2016 | Chang et al. |
| 9,271,925 B2 | 3/2016 | Hammerick |
| 9,295,547 B2 | 3/2016 | Costello et al. |
| 9,308,358 B2 | 4/2016 | Oliver et al. |
| 9,308,361 B2 | 4/2016 | Muni et al. |
| 9,320,876 B2 | 4/2016 | Ressemann et al. |
| 9,333,220 B2 | 5/2016 | Tijsma et al. |
| 9,333,365 B2 | 5/2016 | Zhao |
| 9,351,750 B2 | 5/2016 | Muni et al. |
| 9,398,966 B2 | 7/2016 | Thompson |
| 9,402,719 B2 | 8/2016 | Lane |
| 9,427,343 B2 | 8/2016 | Bogert |
| 9,456,897 B2 | 8/2016 | Krivoruchko et al. |
| 9,498,239 B2 | 11/2016 | Schreck et al. |
| 9,504,556 B2 | 11/2016 | Bebb |
| 9,504,812 B2 | 11/2016 | Edgren et al. |
| 9,561,119 B2 | 2/2017 | Eberhardt et al. |
| 9,597,485 B2 | 3/2017 | Edgren et al. |
| 9,622,850 B2 | 4/2017 | Bebb et al. |
| 9,629,644 B2 | 4/2017 | Schreck et al. |
| 9,649,477 B2 | 5/2017 | Muni et al. |
| 9,662,168 B2 | 5/2017 | Edwards et al. |
| 9,675,451 B2 | 6/2017 | Garde et al. |
| 9,681,914 B2 | 6/2017 | Edwards et al. |
| 9,700,326 B2 | 7/2017 | Morriss et al. |
| 9,707,110 B2 | 7/2017 | McDermott et al. |
| 9,717,612 B2 | 8/2017 | Dorn et al. |
| 10,159,586 B2 * | 12/2018 | Helmick ............... A61F 2/9525 |
| 2007/0208252 A1 | 9/2007 | Makower |
| 2008/0243140 A1 | 10/2008 | Gopferich et al. |
| 2009/0030499 A1 | 1/2009 | Bebb et al. |
| 2009/0270965 A1 | 10/2009 | Sinha et al. |
| 2010/0016946 A1 | 1/2010 | McDermott |
| 2010/0131049 A1 | 5/2010 | Perkins et al. |
| 2010/0204770 A1 | 8/2010 | Mas et al. |
| 2010/0331619 A1 | 12/2010 | Miyoshi et al. |
| 2011/0009951 A1 | 1/2011 | Bogert |
| 2011/0015612 A1 | 1/2011 | Arcand et al. |
| 2011/0054552 A1 | 3/2011 | Takayama et al. |
| 2011/0060214 A1 | 3/2011 | Makower |
| 2011/0118802 A1 | 5/2011 | Usui |
| 2011/0155149 A1 | 6/2011 | Mauch |
| 2011/0270379 A1 | 11/2011 | Bruszewski |
| 2012/0035677 A1 | 2/2012 | Imabayashi et al. |
| 2012/0059454 A1 | 3/2012 | Millwee |
| 2012/0071824 A1 | 3/2012 | Chang et al. |
| 2013/0006055 A1 | 1/2013 | Goldfarb et al. |
| 2013/0035739 A1 | 2/2013 | Goto |
| 2013/0165873 A1 | 6/2013 | Morriss et al. |
| 2013/0231529 A1 | 9/2013 | Chang et al. |
| 2013/0253564 A1 | 9/2013 | Edgren et al. |
| 2013/0261388 A1 | 10/2013 | Jenkins et al. |
| 2013/0282113 A1 | 10/2013 | Punga et al. |
| 2013/0304196 A1 | 11/2013 | Kelly |
| 2013/0310780 A1 | 11/2013 | Phillips |
| 2013/0310781 A1 | 11/2013 | Phillips et al. |
| 2013/0324970 A1 | 12/2013 | Arcand et al. |
| 2014/0012075 A1 | 1/2014 | Konstorum |
| 2014/0031852 A1 | 1/2014 | Edgren et al. |
| 2014/0031917 A1 | 1/2014 | Thompson |
| 2014/0074140 A1 | 3/2014 | Johnson et al. |
| 2014/0074141 A1 | 3/2014 | Johnson et al. |
| 2014/0079755 A1 | 3/2014 | Eaton |
| 2014/0107763 A1 | 4/2014 | Layne et al. |
| 2014/0107766 A1 | 4/2014 | Banas et al. |
| 2014/0154236 A1 | 6/2014 | Hester et al. |
| 2014/0200444 A1 | 7/2014 | Kim et al. |
| 2014/0222144 A1 | 8/2014 | Eberhardt et al. |
| 2014/0276408 A1 | 9/2014 | Abbate |
| 2014/0276654 A1 | 9/2014 | Jenkins |
| 2014/0296898 A1 | 10/2014 | Chang et al. |
| 2014/0330372 A1 | 11/2014 | Weston et al. |
| 2014/0336693 A1 | 11/2014 | Goldfarb et al. |
| 2014/0336694 A1 | 11/2014 | Becker |
| 2015/0119974 A1 | 4/2015 | Rothstein |
| 2015/0196735 A1 | 7/2015 | Olig et al. |

\* cited by examiner

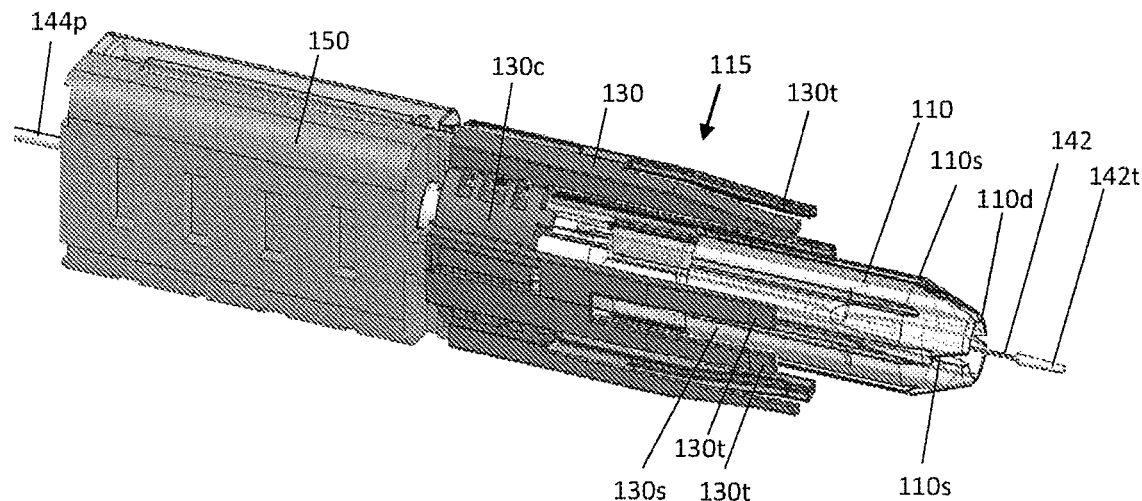
FIG. 7
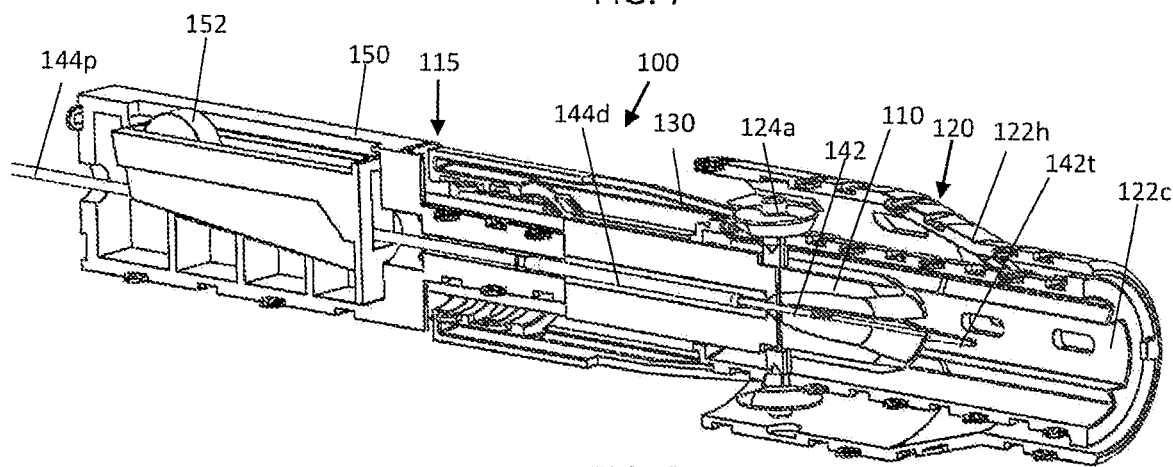
FIG. 8A
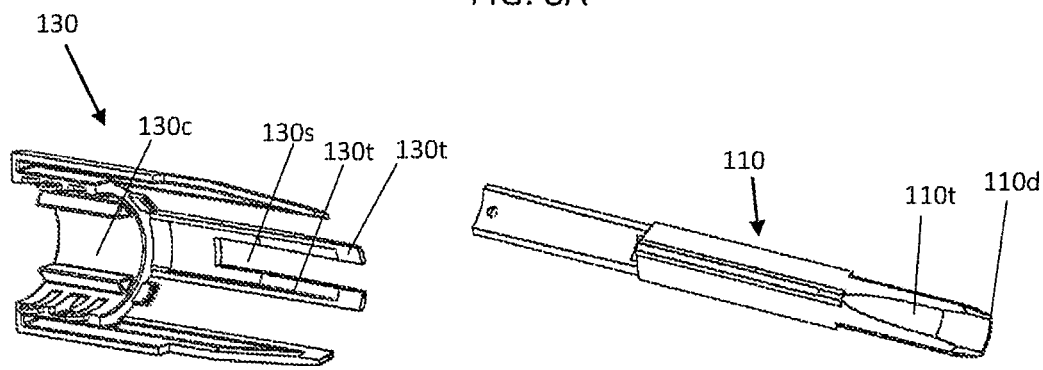
FIG. 8B
FIG. 8C

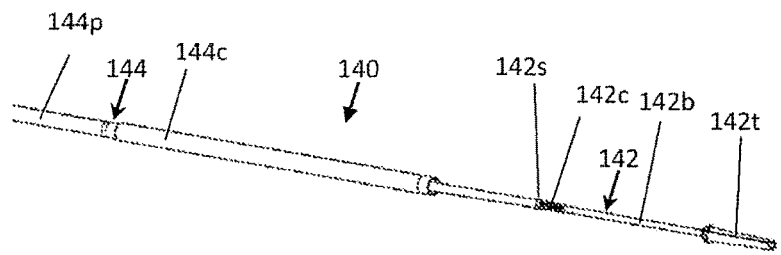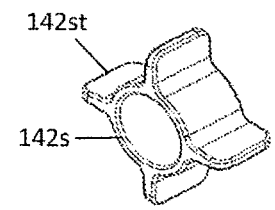
FIG. 9A
FIG. 9B
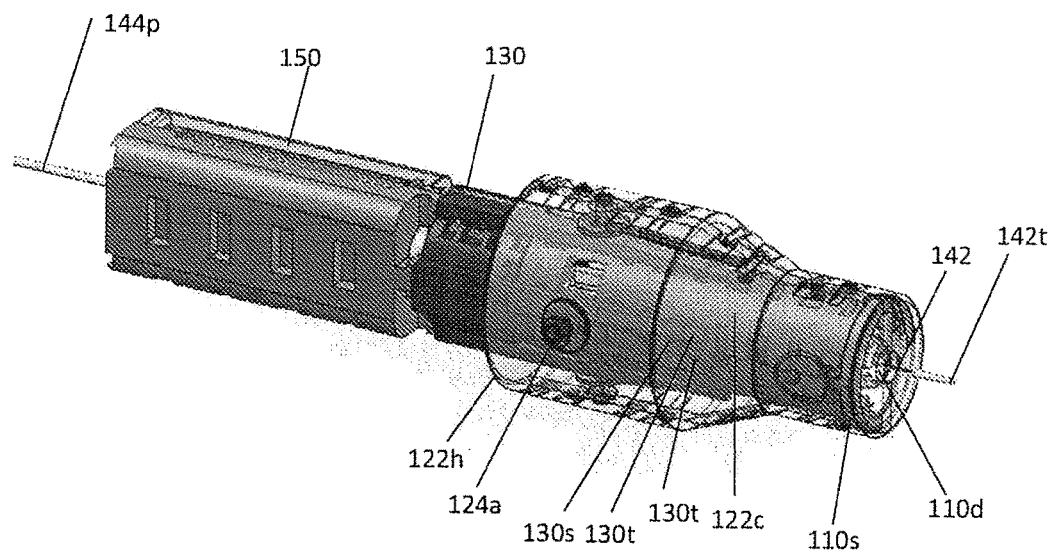
FIG. 10
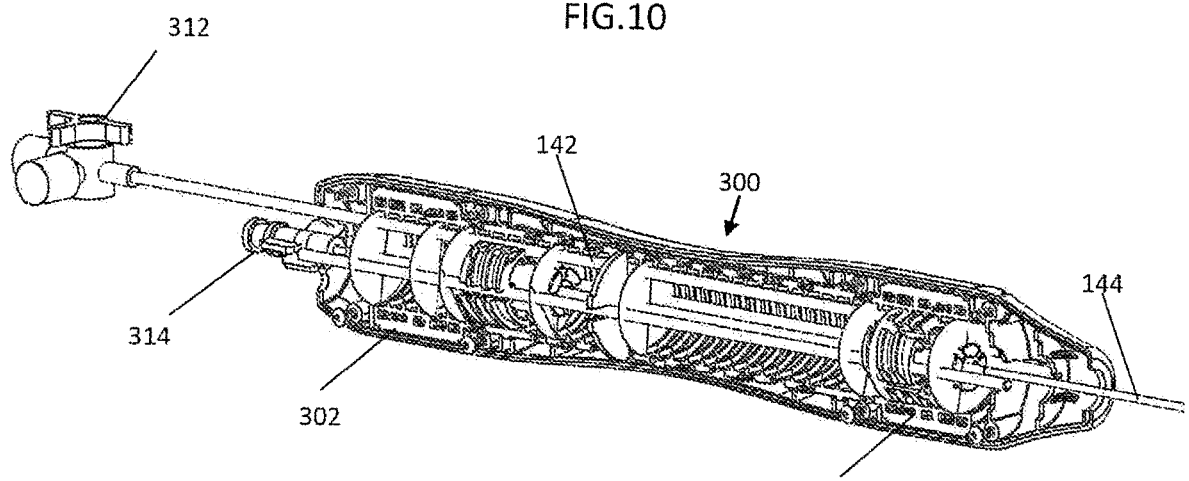
FIG. 11

SCAFFOLD LOADING AND DELIVERY SYSTEMS

CROSS-REFERENCE TO RELATED APPLICATIONS

This application claims the benefit of U.S. Provisional Application No. 62/273,188 filed Dec. 30, 2015 and entitled Scaffold Loading and Delivery Systems which is hereby incorporated by reference in its entirety.

FIELD OF THE DISCLOSURE

This disclosure pertains, inter alia, to scaffold loading and delivery devices, assemblies, systems and methods of using the same.

BACKGROUND

A variety of medical conditions are treatable by the implantation of expandable devices into natural body lumens. For example, it is commonplace to implant stents into the vasculature of diseased patients to mitigate the risks associated with vessel stenosis. Other examples of conventional tubular medical implants include woven grafts and stent-grafts that are used to span vascular aneurysms, expandable devices that are used to bypass strictures in the ureter and urethra, and stents that are used in the peripheral vasculature, prostate, sinus, airways, and esophagus, among others.

While biostable and biodegradable polymeric stents have been proposed to address the limitations of metallic stents, including potential issues with thrombosis, chronic injury, and vascular remodeling, their use has been limited by the fact that polymeric stents may undergo stress relaxation if left in a crimped delivery configuration for an extended period of time, such as during shipping and storage.

There is a continuing need for devices and systems that offer the possibility of loading polymeric tubular implants into a delivery system by a healthcare professional just prior to implantation, thereby avoiding the possibility that the implant undergo stress relaxation during shipping and/or storage in a loaded or crimped configuration.

SUMMARY

In various aspects, the present disclosure provides a loading system that includes (a) a delivery catheter, (b) a loading assembly that includes (i) a funnel assembly that includes a tapered funnel structure, and optionally, a pin lift, a clamp and/or a body portion and (ii) a loading aid assembly that includes a receptacle, a plurality of loading pins and, optionally, a self-expanding scaffold. When a self-expanding scaffold is provided within the loading aid assembly, the self-expanding scaffold may be held within the receptacle via the loading pins and may be used to longitudinally guide the self-expanding scaffold into the tapered funnel structure of the funnel assembly, which provides a funnel shape for crimping the scaffold. In various embodiments, the optional clamp may be used to secure the funnel assembly to the delivery catheter and/or the optional pin lift may be used to retract the loading pins from the scaffold. In various embodiments, the optional body portion may be used to maintain the clamp, tapered funnel and pin lift in a single structure.

In various aspects, the present disclosure provides a loading assembly that comprises: (a) a funnel assembly comprising a tapered funnel structure having a distal end and a proximal end and comprising (i) a loading lumen having a loading axis, an open distal end, an open proximal end, and at least one tapered region having a distal end with a first diameter and a proximal end with a second diameter that is smaller than the first diameter and (ii) a slotted wall surrounding the loading lumen that has a plurality of longitudinal slots formed therein, the slots having an open distal end; and (b) a loading aid assembly comprising (i) a receptacle comprising a receptacle wall, a receptacle lumen having a least one open receptacle lumen end and a receptacle axis, (ii) a scaffold comprising a scaffold wall and having a scaffold axis, a proximal scaffold end, a distal scaffold end, an inner luminal surface and an outer abluminal surface, (iii) a plurality of loading pins comprising loading pin shafts that extend from the receptacle wall, into the receptacle lumen and through the scaffold wall, the pins holding the scaffold within the receptacle lumen in a position in which the scaffold axis is coaxial with the receptacle axis. The loading aid assembly is configured to receive the distal end of the tapered funnel structure within the receptacle lumen via the open receptacle lumen end, such that the scaffold is at least partially positioned in the loading lumen, such that at least a portion of the tapered funnel structure wall is positioned between the outer abluminal surface of the stent and the inner luminal surface of the receptacle wall, such that the loading pins are positioned within the longitudinal slots of the tapered funnel structure, and such that longitudinal movement of the loading aid assembly in a proximal direction relative to the funnel assembly results in proximal longitudinal movement of the loading pins within the slots of the tapered funnel structure and proximal longitudinal movement of at least the proximal scaffold end into the tapered region thereby reducing at least a portion of the diameter of the same.

In various embodiments, which may be used in conjunction with any of the preceding aspects and embodiments, the loading pins may comprise (a) a loading pin shaft that extends through an aperture in the receptacle wall and into the receptacle lumen and (b) an enlarged portion positioned on a side of the receptacle wall opposite the receptacle lumen, the enlarged portion having a width that is greater than a width of the aperture. In certain of these embodiments, the receptacle may comprise first and second walls separated by a gap and wherein the enlarged portions of the pins are positioned in the gap between the walls.

In various embodiments, which may be used in conjunction with any of the preceding aspects and embodiments, the loading aid assembly may further comprise springs that bias the loading pins toward the receptacle axis.

In various embodiments, which may be used in conjunction with any of the preceding aspects and embodiments, the loading assembly may comprise a stop that limits the proximal longitudinal movement of the loading pin shafts within the slots of the tapered funnel structure. In certain of these embodiments, removal of the loading pin shafts from the scaffold wall and the slots allows additional longitudinal movement of the loading aid assembly in a proximal direction relative to the funnel assembly, in which case the receptacle may be configured to compress and close the slots of the tapered funnel structure upon the additional longitudinal movement, if desired.

In various embodiments, which may be used in conjunction with any of the preceding aspects and embodiments, the loading assembly may comprise a pin lift having a radially tapered surface, such that relative longitudinal movement between the radially tapered surface of the pin lift and the loading pins may engage the loading pins and move the loading pins radially away from the receptacle axis. In certain of these embodiments, the pin lift may be part of the funnel assembly and distal longitudinal movement of the radially tapered surface of the pin lift relative to the loading pins engages the loading pins and moves the loading pins radially away from the receptacle axis. Alternatively or in addition, the loading pins may comprise (a) a loading pin shaft that extends through an aperture in the receptacle wall and into the receptacle lumen and (b) an enlarged portion positioned on a side of the receptacle wall opposite the receptacle lumen and having a width that is greater than a width of the aperture, such that distal longitudinal movement of the pin lift relative to the loading pins causes the tapered surface of the pin lift to engage the enlarged portions of the loading pins and move the loading pins radially away from the receptacle axis. For this purpose, the pin lift may comprise, for example, a plurality of tapered projections each pair forming a slot therebetween which is configured to receive the loading pin shafts.

In various embodiments, which may be used in conjunction with any of the preceding aspects and embodiments, the funnel assembly may further comprise a clamp for positioning a delivery sheath of a catheter in a position such that the delivery sheath is positioned to receive the scaffold from the loading lumen.

In some aspects, the disclosure provides a loading system that comprises (a) a loading assembly in accordance with any of the above aspects and embodiments, and (b) a catheter that comprises: (i) an outer sheath comprising an outer sheath lumen and having a proximal outer sheath end and a distal outer sheath end and (ii) an inner member having an inner member proximal end and an inner member distal end and comprising an elongate shaft and an enlarged diameter portion near the inner member distal end, at least a portion of the elongate inner member being disposed within the outer sheath.

In some embodiments, the outer sheath and the inner member of the catheter are positioned relative to the tapered funnel structure such that the distal end of the outer sheath lumen is in communication with the loading lumen and such that the elongate inner member extends beyond the distal end of the outer sheath and at least partially though the tapered region of the loading lumen.

In some embodiments, proximal longitudinal movement of the loading aid assembly relative to the funnel assembly proceeds to a point where the loading pins reach a stop, resulting in a reduction in diameter of at least a proximal portion of the scaffold and in the scaffold being disposed around the enlarged diameter portion of the inner elongate member. In certain instances, the loading system may include a handle that independently proximally retracts the inner elongate member and outer sheath. In certain instances, removal of the loading pin shafts from the slots and further proximal longitudinal movement of the loading aid assembly beyond the point where the loading pins reach a stop, may cause compression of the tapered funnel structure such that the slots close, such that the inner diameter of the tapered region is reduced, and such that proximal movement of the inner elongate member causes the enlarged diameter portion of the inner elongate member to engage the scaffold and draw the scaffold into outer sheath. For example, an inner luminal surface of the receptacle wall may be tapered for this purpose, such that the slots close and the diameter of the tapered region is reduced upon the further proximal longitudinal movement of the loading aid assembly.

In other aspects, the disclosure provides a catheter that comprises: (a) an outer sheath comprising an outer sheath lumen and having a proximal outer sheath end and a distal outer sheath end and (b) an inner member having an inner member proximal end and an inner member distal end and comprising an elongate shaft and an enlarged diameter portion near the inner member distal end that comprises a hub and a plurality of radial projections extending from the hub, the inner member being disposable within the outer sheath.

In some embodiments, the inner member may further comprise a braid reinforced tube, a wound wire coil and a tapered distal tip.

Alternatively or in addition, the outer sheath may comprises a proximal shaft and an outer distal capsule.

In other aspects, the disclosure provides a method of crimping a tubular self-expanding scaffold using the loading assembly in accordance with any of the above aspects and embodiments, the method comprising: (a) joining the loading aid assembly with the funnel assembly, such that the distal end of the tapered funnel structure is positioned within the receptacle lumen, such that the scaffold is at least partially positioned in the loading lumen, such that at least a portion of the tapered funnel structure wall is positioned between the outer abluminal surface of the stent and the inner luminal surface of the receptacle wall, and such that the loading pins are positioned within the longitudinal slots of the tapered funnel structure; and (b) generating longitudinal movement of the loading aid assembly in a proximal direction relative to the funnel assembly such that the loading pins undergo proximal longitudinal movement within the slots of the tapered funnel structure and such that at least the proximal scaffold end undergoes proximal longitudinal movement into the tapered region, thereby reducing at least a portion of the diameter of the scaffold.

In certain embodiments, the method further comprises removing the loading pin shafts from the scaffold wall and the slots. In certain of these embodiments, the method additionally comprises generating further longitudinal movement of the loading aid assembly in a proximal direction relative to the funnel assembly, wherein an inner luminal surface of the receptacle wall is tapered such that the receptacle compresses and closes the slots of the tapered funnel structure as a result of the further longitudinal movement.

In various embodiments, which may be used in conjunction with any of the preceding aspects and embodiments, the funnel assembly may be attached to a delivery sheath of a catheter such that the delivery sheath is positioned to receive the scaffold from the loading lumen.

In various embodiments, which may be used in conjunction with any of the preceding aspects and embodiments, (a) the funnel assembly may be attached to a catheter that comprises (i) an outer sheath comprising an outer sheath lumen and having a proximal outer sheath end and a distal outer sheath end and (ii) an inner member having an inner member proximal end and an inner member distal end and comprising an elongate shaft and an enlarged diameter portion near the inner member distal end, at least a portion of the elongate inner member being disposed within the outer sheath, (b) the outer sheath and the inner member may be positioned relative to the tapered funnel structure such that the distal end of the outer sheath lumen is in communication with the loading lumen and such that the elongate inner member extends beyond the distal end of the outer sheath and at least partially though the tapered region of the loading lumen, and (c) the longitudinal movement of the loading aid assembly in a proximal direction relative to the funnel assembly may cause the scaffold to be disposed around the enlarged diameter portion of the inner elongate member and reduce at least a portion of the diameter of the scaffold that is disposed around the inner elongate member into engagement with the enlarged diameter portion of the inner elongate member. In such embodiments, the method may further comprise proximally moving the inner elongate member relative to the outer sheath, thereby drawing the scaffold into the outer sheath lumen.

The above and other aspects and embodiments of the present disclosure will become immediately apparent to those of ordinary skill in the art upon review of the detailed description and claims to follow.

BRIEF DESCRIPTION OF THE DRAWINGS

FIG. 7 is a schematic perspective view of a funnel assembly in accordance with the present disclosure.

FIG. 8A is a schematic cutaway perspective view a loading system in accordance with the present disclosure.

FIG. 8B is a schematic perspective view of one half of pin lift in accordance with the present disclosure.

FIG. 8C is a schematic perspective view of one quarter of a tapered funnel structure in accordance with the present disclosure.

FIG. 9A is a schematic perspective view illustrating a catheter in accordance with the present disclosure.

FIG. 9B is a schematic perspective view illustrating a scaffold lock in accordance with the present disclosure.

FIG. 10 is a schematic perspective view of a loading system in accordance with the present disclosure.

FIG. 11 is a schematic cutaway view of a delivery catheter handle.

DETAILED DESCRIPTION

Figure 1A:
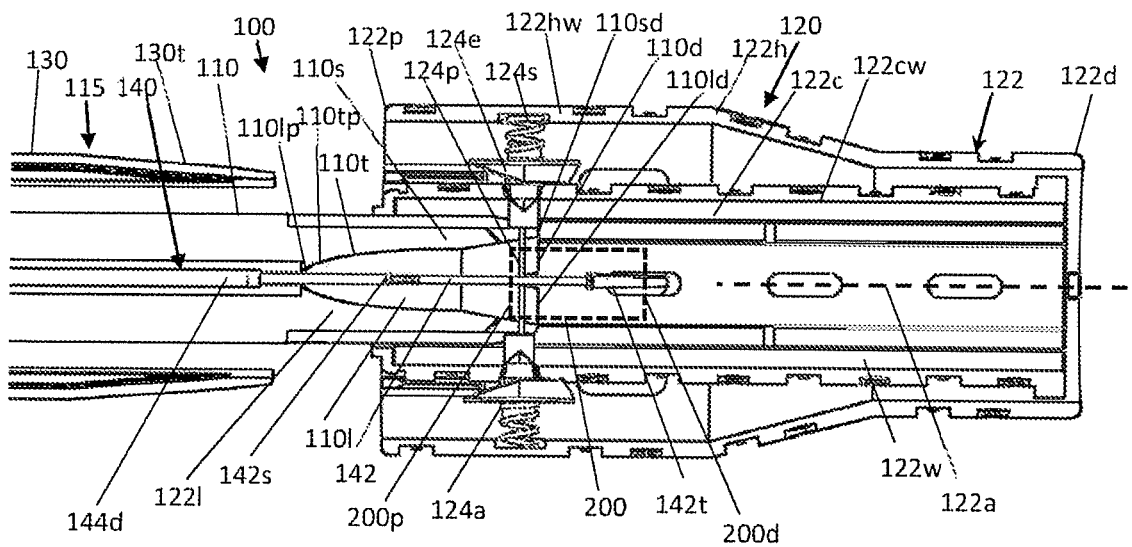
FIGS. 1A and 1B are schematic cutaway views in line format and shaded format, respectively, of a delivery system in accordance with the present disclosure at a first stage in a scaffold loading process.

The devices, assemblies and systems described herein are useful for loading, delivery and deployment of self-expanding scaffolds into bodily lumens.

The implantable scaffolds loaded and delivered by delivery systems of the present disclosure are generally tubular devices, which are self-expanding devices in various embodiments. As used herein, "device," "scaffold," "stent" and "implant" may be used synonymously. Also as used herein, "self-expanding" is intended to include devices that are crimped to a reduced delivery configuration for delivery into the body, and thereafter tend to expand to a larger suitable configuration once released from the delivery configuration. As used herein "strands" and "filaments" may be used interchangeably and include single fiber strands and filaments (also referred to as monofilaments) and multi-fiber strands and filaments. As used herein a "sheath," "tube," "hollow member," "catheter" and "tubular member" may be used synonymously.

Scaffolds for use in conjunction with the present disclosure are typically tubular devices which may be of various sizes, including a variety of diameters and lengths, and which may be used for a variety of applications. Various scaffold embodiments of the present disclosure are self-expanding in that they are manufactured at a first diameter, subsequently reduced or "crimped" to a second reduced diameter for placement within a delivery catheter, and self-expand towards the first diameter when extruded from the delivery catheter at an implantation site. Scaffolds for use in the present disclosure may be formed from a variety of polymeric and non-polymeric materials. Scaffolds for use in the present disclosure may be biodegradable or non-biodegradable, or be a combination of both biodegradable and non-biodegradable materials. In various embodiments, the implantable scaffolds may comprise a generally tubular structure comprising scaffolding material. Scaffolds for use in the present disclosure may be fiber-based or non-fiber-based. In various embodiments, scaffolds for use in the present disclosure are braided scaffolds.

In one aspect the present disclosure describes loading systems that include (a) a delivery catheter, (b) a loading assembly that includes (i) a funnel assembly that includes a tapered funnel structure, and optionally, a pin lift, a clamp and/or a body portion and (ii) a loading aid assembly that includes a receptacle, a plurality of loading pins and, optionally, a self-expanding scaffold. The loading aid assembly holds the self-expanding scaffold within the receptacle via the loading pins and is used to longitudinally guide the self-expanding scaffold into the tapered funnel structure of the funnel assembly. The funnel assembly is typically attached to the distal end of the delivery catheter. A clamp, such as a roller clamp, can be used to secure the funnel assembly to the delivery catheter, the tapered funnel structure within the funnel assembly provides a funnel shape for crimping the scaffold. Where provided, the pin lift retracts the loading pins from the scaffold, and the main body can be used to maintain the clamp, tapered funnel and pin lift in a single structure.

Figure 1B:
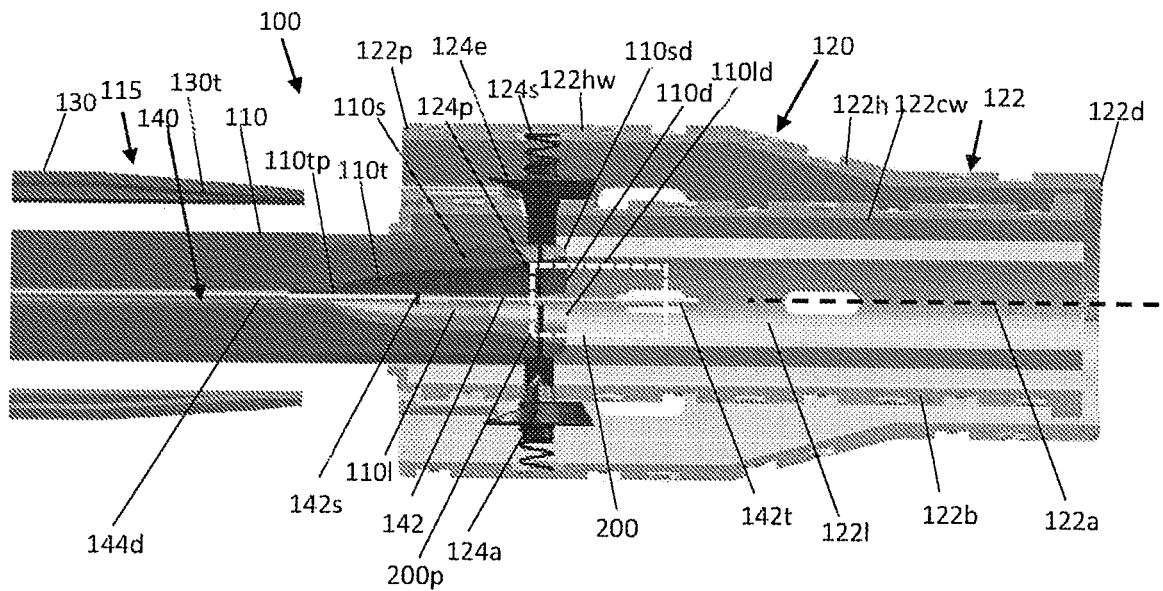
Figure 1C:
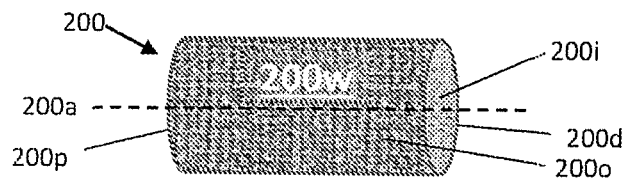
FIG. 1C is a schematic illustration of a scaffold.

With reference now to FIGS. 1A-1C, a partial schematic cutaway view of loading system in accordance with the present disclosure is shown. The loading system includes (a) a catheter 140, (a) a funnel assembly that includes a tapered funnel structure 110 and a pin lift 130 (as well as a body portion and a roller clamp as discussed further below) and (c) a loading aid assembly 120 that includes a receptacle 122, a cylindrical scaffold 200 and a plurality of loading pin assemblies 124a.

The tapered funnel structure 110 has a distal end 110d and a proximal end (not shown) and includes (i) a plurality of longitudinal slots 110s formed therein (the face of slot 110s is identified in FIGS. 1A and 1B), the slots 110s having an open distal end 110sd and (ii) a loading lumen 110l having a loading axis (coincident with axis 122a), a lumen distal end 110*ld*, a lumen proximal end 110*lp* and at least one tapered region 110*t* having a tapered region distal end (in this case, corresponding to the distal end 110*ld* of the loading lumen 110*l*) with a first diameter and having a tapered region proximal end 110*tp* with a second diameter that is smaller than the first diameter.

The loading aid assembly 120 comprises the following: (i) a receptacle 122 having a receptacle axis 122*a* and having a receptacle wall 122*w* and a receptacle lumen 122*l* having an open proximal end and, (ii) a cylindrical scaffold 200 comprising (see FIG. 1C) a scaffold wall 200*w* and having a scaffold axis 200*a*, a proximal scaffold end 200*p*, a distal scaffold end 200*d*, an inner luminal surface 200*i* and an outer abluminal surface 200*o*, (iii) a plurality (four shown) of loading pin assemblies 124*a* comprising enlarged loading pin caps 124*e* and pin shafts 124*p* that extend from the receptacle wall, into the receptacle lumen 122*l* and through the scaffold wall 200*w* (e.g., through a diamond-shaped aperture in a braided stent or through a cell of another closed cell stent design, etc.). The loading pin assemblies 124*a* hold the scaffold 200 within the receptacle lumen 122*l* and in a position such that the scaffold axis 200*a* is coaxial with the receptacle axis 122*a*. In the embodiment shown, the receptacle 122 is formed from two components: an outer housing 122*h* having an outer housing wall 122*hw* and an inner collar 122*c* having an inner collar wall 122*cw*. The loading pin shafts 124*p* extend through the inner collar wall 122*cw*. The loading pin assemblies 124*a* in the embodiment shown are further provided with loading pin springs 124*s*, which are disposed between the housing wall 120*aw* and the enlarged loading pin heads 124*e*, bias the pin shafts 124*p* toward the receptacle axis 122*a*. Due to the loading pin springs 124*s*, the loading pin heads 124*e* are biased against the collar wall 122*cw*.

Figure 5:
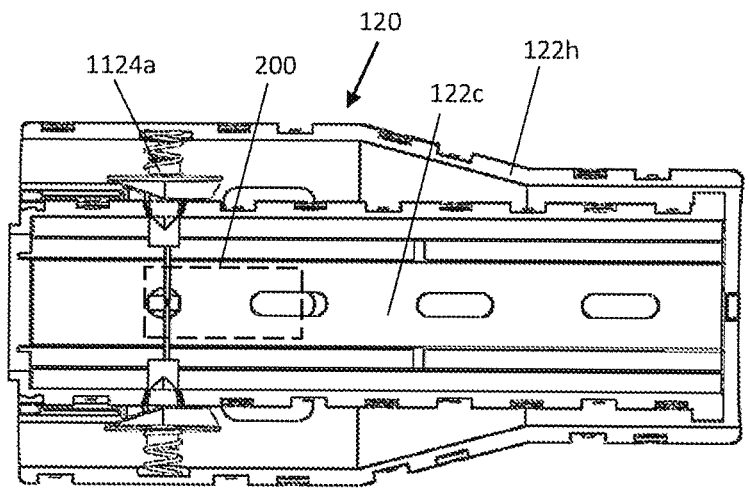
FIG. 5 is a schematic cutaway view of a loading aid assembly in accordance with the present disclosure.

An additional view of the loading aid assembly 120 is provided in FIG. 5, which shows the outer housing 122*h*, inner collar 122*c*, loading pin assemblies 124*a* and scaffold 200. In some cases, a loading aid assembly 120 with a preloaded scaffold 200 of this type may be pre-constructed, packaged and sterilized for use by a health care professional.

Figure 6A:
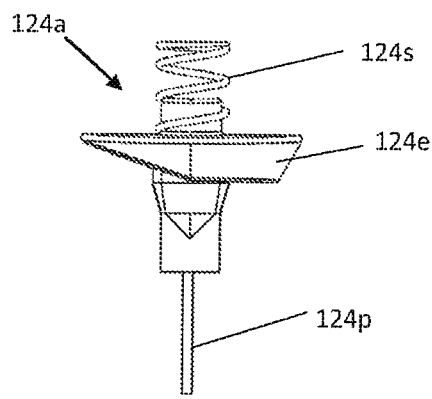
FIG. 6A is a schematic side view of a pin assembly in accordance with the present disclosure.
Figure 6B:
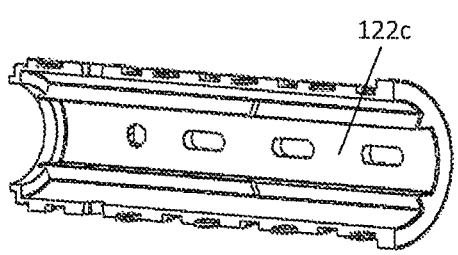
FIG. 6B is a schematic perspective view of one half of an inner collar in accordance with the present disclosure.
Figure 6C:
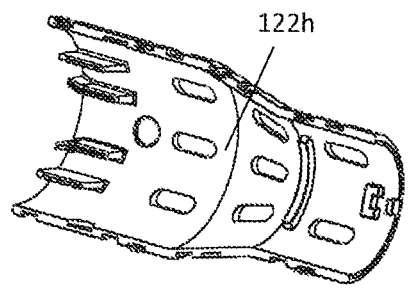
FIG. 6C is a schematic perspective view of one half of an outer housing in accordance with the present disclosure.

Further detail of a loading pin assembly 124*a* is provided in FIG. 6A, which shows the pin shaft 124*p*, enlarged loading pin cap 124*e* and loading pin spring 124*s* of the loading pin assembly 124*a*. Further detail of one half of the inner collar 122*c* is shown in the perspective view in FIG. 6B. Further detail of one half of the outer housing 122*h* is shown in the perspective view in FIG. 6C.

Further detail of the catheter 140 provided in FIGS. 1A and 1B is provided in FIG. 9A, which shows an outer sheath 144 that includes a proximal shaft 144*p* and an outer distal capsule 144*d*. Thus, in the embodiment shown, the outer sheath 144 is a composite design consisting of outer distal capsule 144*d* for scaffold encapsulation and a smaller diameter outer proximal shaft 144*p*. The outer distal capsule 144*d* may include a liner such as a fluoropolymer (e.g., polytetrafluoroethylene) liner for lubricity and a braid reinforced tube for radial strength. The outer proximal shaft 144*p* may include a braid reinforced tube and a tightly wound wire coil for compression resistance. Such a composite design provides tensile and compression resistance while maintaining flexibility. The outer proximal shaft 144*p* may further be designed to enable contrast injection through an introducer sheath while the delivery system is in place, for example, to allow for anatomical landmarking. The catheter 140 of FIG. 9A also shows an inner member 142 that includes a braid reinforced tube 142*b*, tightly wound wire coil 142*c*, a tapered distal tip 142*t* and a scaffold lock 142*s*. The braid reinforced tube 142*b* and tightly wound coil 142*c* provide compression resistance and tensile strength while maintaining flexibility. An axial wire (not shown) may be incorporated into the wall of the inner member 142 to further increase tensile strength. The distal tip 142*t* has an atraumatic nosecone as a tapered distal tip 142*t* to facilitate tracking over a guidewire through tight anatomy and to prevent vessel trauma. The scaffold lock 142*s* is attached to the inner member 142 near the distal end.

Additional detail of the scaffold lock 142*s* is provided in FIG. 9B. The tines 142*st* of the scaffold lock 142*s* may fit, for example, into diamonds of a braided scaffold (or a cell of another scaffold design) and secure the scaffold during capture and deployment. Multiple scaffold locks may be used. Alternatively or in addition, another scaffold securement feature such as a polymeric pad may be used for scaffold securement.

The pin lift 130 shown in FIGS. 1A and 1B includes a plurality of tapered distal projections 130*t*. A funnel assembly 115 comprising a body portion 150, clamp (not shown), pin lift 130 and tapered funnel structure 110, along with a catheter (outer proximal shaft 144*p*, inner member 142 and tapered distal tip 142*t* shown), is shown in perspective view of FIG. 7. As further seen from FIG. 7, the pin lift includes a collar 130*c* from which four pairs of tapered projections 130*t* extend distally, each pair of tapered projections of 130*t* forming a slot 130*s*. Also shown in FIG. 7 are the slots 110*s* (four total) of the tapered funnel structure 110. The pin lift 130 and tapered funnel structure 110 are supported by the body portion 150.

A further view provided in FIG. 8A shows a delivery system 100 comprising a catheter (outer proximal shaft 144*p*, outer distal capsule 144*d*, inner member 142 and tapered distal tip 142*t* numbered), a funnel assembly 115 (including a body portion 150 with roller clamp 152 for holding the catheter in place, a pin lift 130, and a tapered funnel structure 110), and loading aid assembly 120 (including outer housing 122*h*, inner collar 122*c*, loading pin assemblies 124*a* and scaffold) (scaffold not shown).

Further detail of one half of the pin lift 130 (tapered projections 130*t* and slot 130*s* also numbered) is provided in the perspective view in FIG. 8B. Further detail of one quarter of the tapered funnel structure 110 (distal end 110*d* and tapered region 110*t* also numbered) is provided in the perspective view in FIG. 8C.

Turning back to FIGS. 1A and 1B, the loading aid assembly 120 is configured to be placed over the tapered funnel structure 110 of the funnel assembly 115 such that the scaffold 200 is guided into the distal end 110*ld* of the loading lumen 110*l*. During this process, the loading aid assembly 120 receives the distal end 110*d* of the tapered funnel structure 110 within the receptacle lumen 122*l* via the lumen opening at the proximal receptacle end 122*p*, such that longitudinal movement of the loading aid assembly 120 in a proximal direction relative to the funnel assembly results in proximal longitudinal movement of the loading pin shafts 124*p* into the slots 110*s* of the tapered funnel structure 110 and in proximal longitudinal movement of the proximal end 200*p* of the scaffold 200 into the loading lumen 110*l*.

Figure 2A:
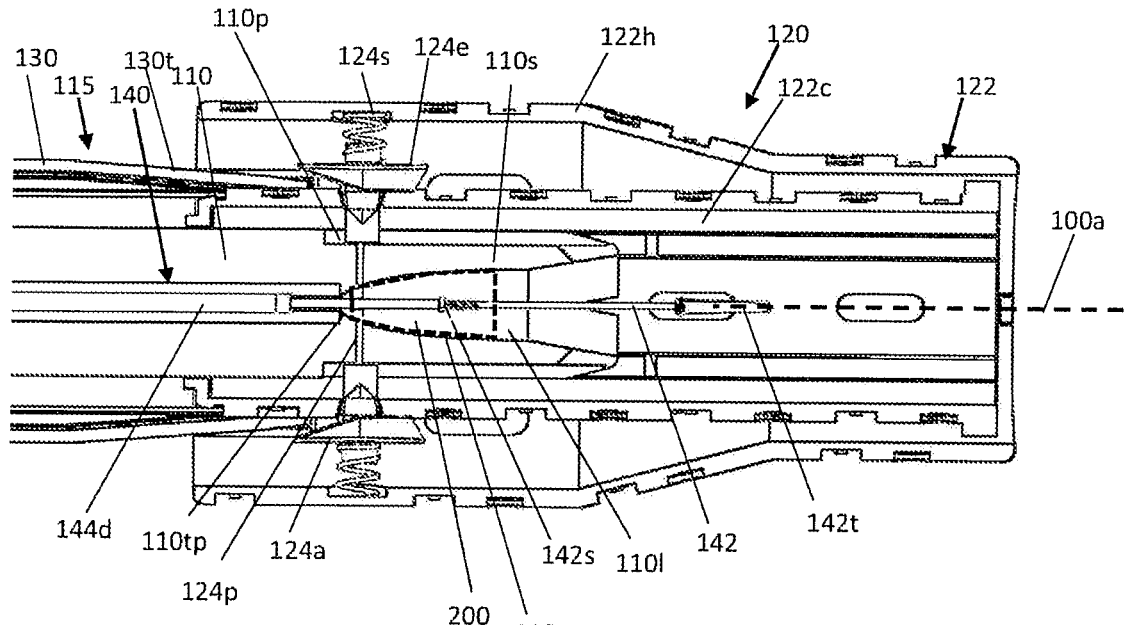
FIGS. 2A and 2B are schematic cutaway views in line format and shaded format, respectively, of a delivery system in accordance with the present disclosure at a second stage in a scaffold loading process.
Figure 2B:
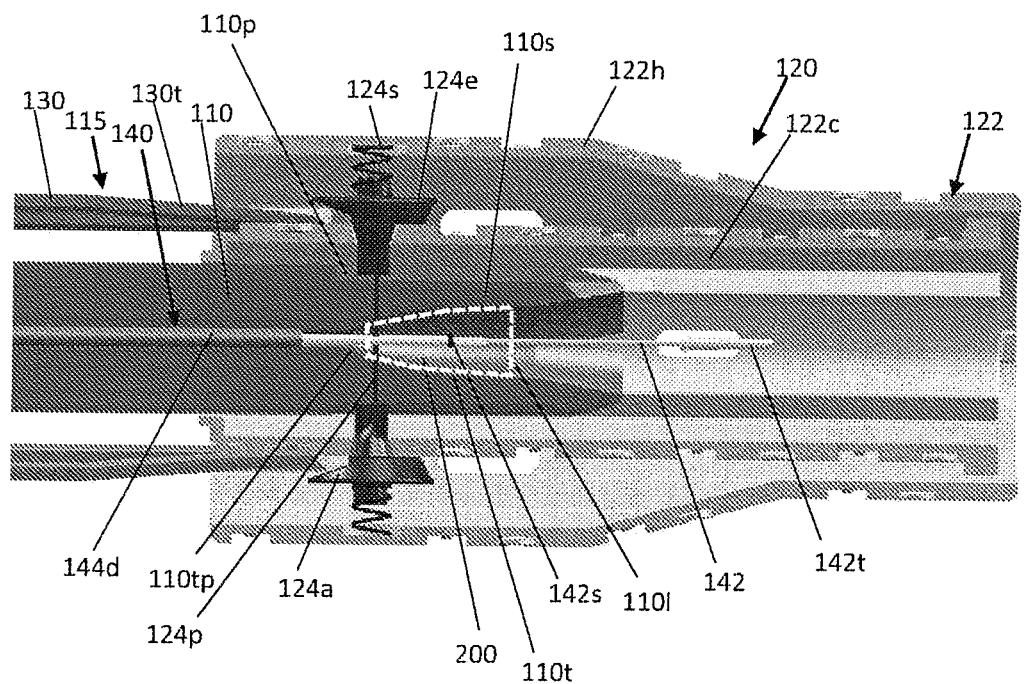

Turning now to FIGS. 2A and 2B, further longitudinal movement of the loading aid assembly 120 in a proximal direction relative to the funnel assembly 115 results in further proximal longitudinal movement of the loading pin shafts 124*p* into the slots 110*s* of the tapered funnel structure 110 and further proximal longitudinal movement of the scaffold 200 into the loading lumen 110*l* up to a point where the loading pin shafts 124*p* engage stops 110*p* associated with the slots 110s of the tapered funnel structure 110, thereby stopping the proximal progress of the loading aid assembly 120 relative to the funnel assembly 115. At this point, the proximal end 200p of the scaffold 200 has been crimped to a diameter almost equivalent to the inner diameter of the outer distal capsule 144d.

Figure 3A:
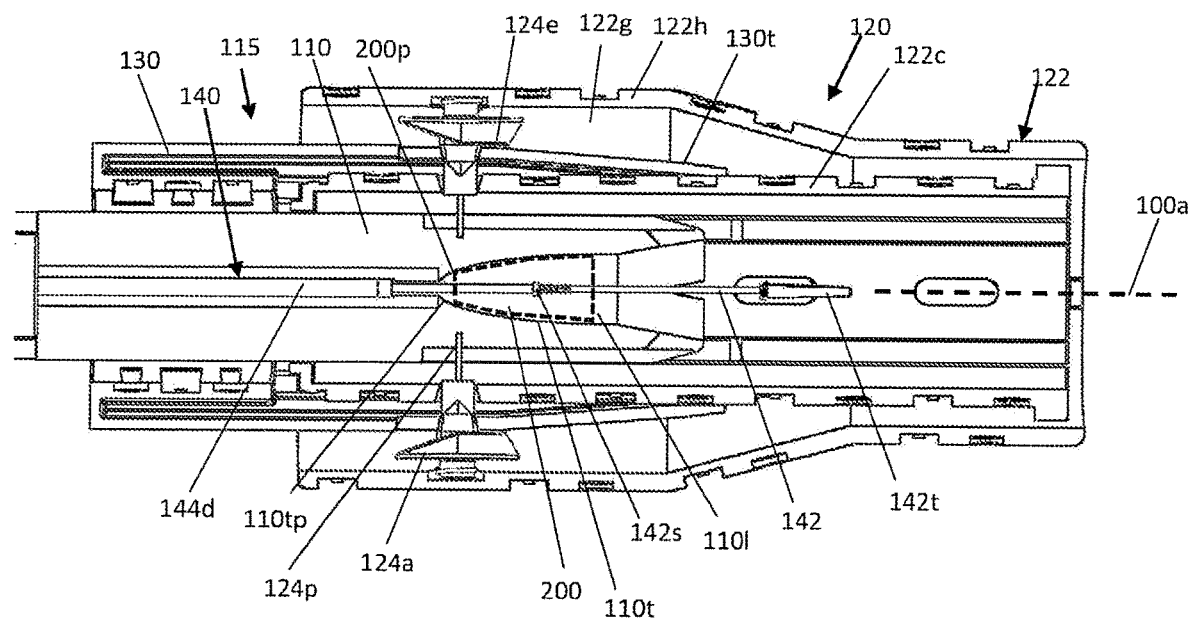
FIGS. 3A and 3B are schematic cutaway views in line format and shaded format, respectively, of a delivery system in accordance with the present disclosure at a third stage in a scaffold loading process.
Figure 3B:
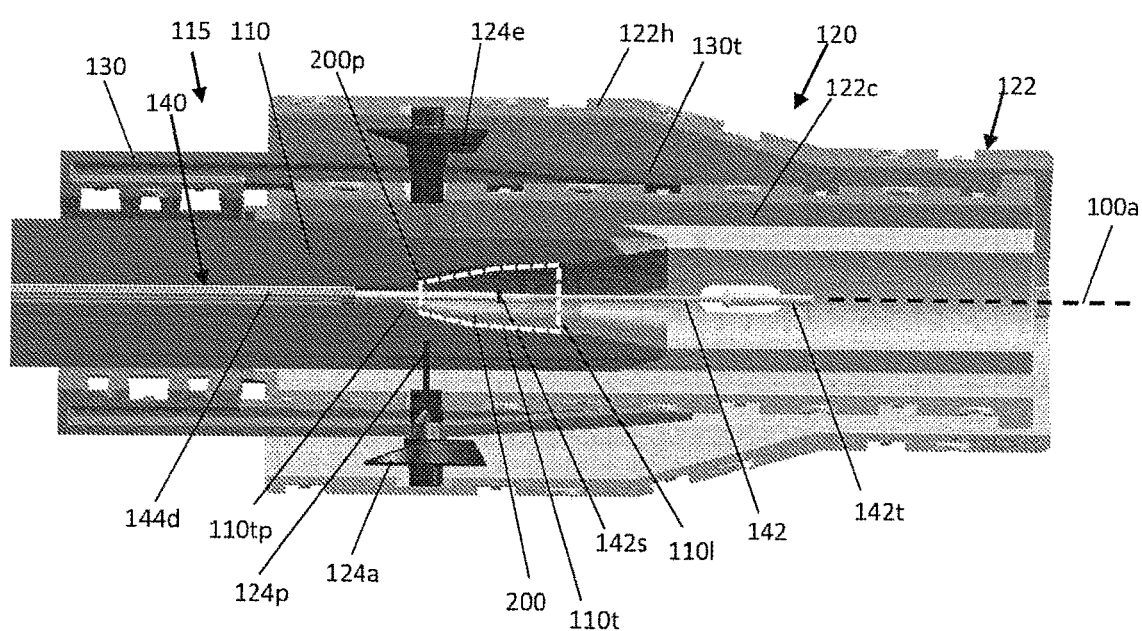

In a next step, and with reference to FIGS. 3A and 3B, the pin lift 130 is pushed distally forward into a gap 122g between the inner collar 122c and outer housing 122h of the loading aid assembly 120. As the pin lift 130 is pushed distally forward, the tapered projections 130t advance on either side of the loading pin shafts 124p, such that the loading pin shafts 124p are positioned in the slots 130s between each pair of projections 130t. As seen in FIGS. 3A and 3B, the enlarged loading pin heads 124e are beveled, allowing the tapered projections 130t to wedge under the enlarged loading pin heads 124e, overcoming the radially inward forces exerted by the pin springs 124s and moving the loading pin shafts 124p radially outward from the center axis 100a of the assembly. Radially outward movement of the loading pin shafts 124p leads to disengagement of the loading pin shafts 124p from the scaffold 200 and removal of the loading pin shafts 124p from the longitudinal slots 110s of the tapered funnel structure 110. A snap feature may be used to lock the collar 130c of the pin lift 130 to the loading aid assembly 120 once the pin lift 130 is distally advanced to a distal-most position relative to the loading aid assembly 120.

Figure 4A:
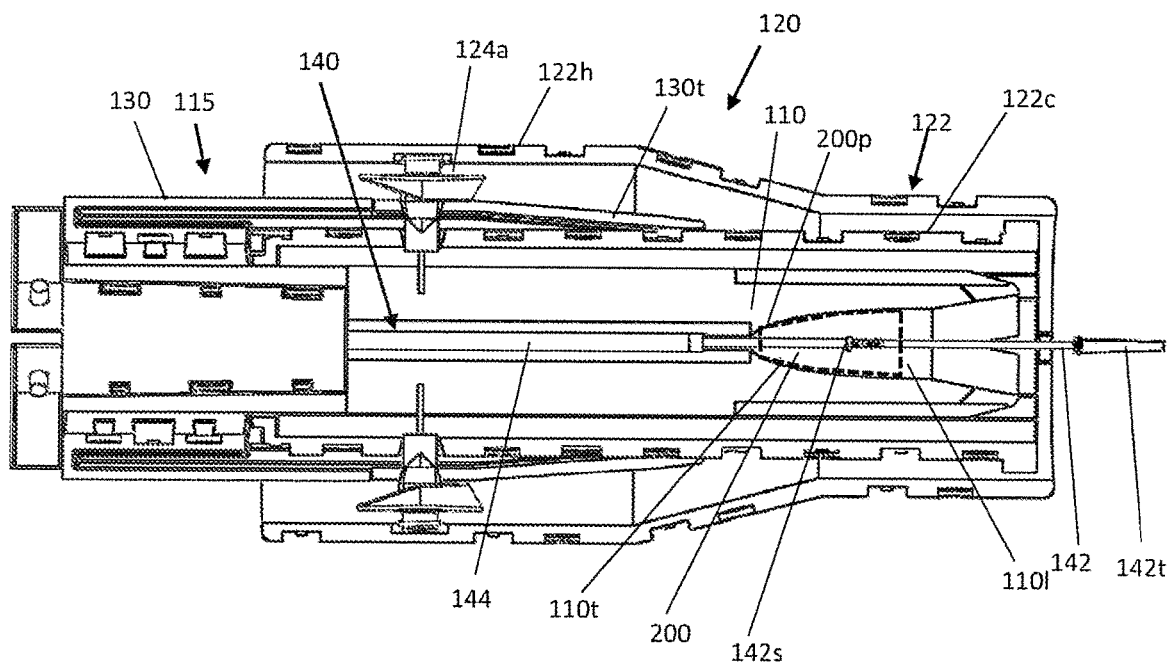
FIGS. 4A and 4B are schematic cutaway views in line format and shaded format, respectively, of a delivery system in accordance with the present disclosure at a fourth stage in a scaffold loading process.
Figure 4B:
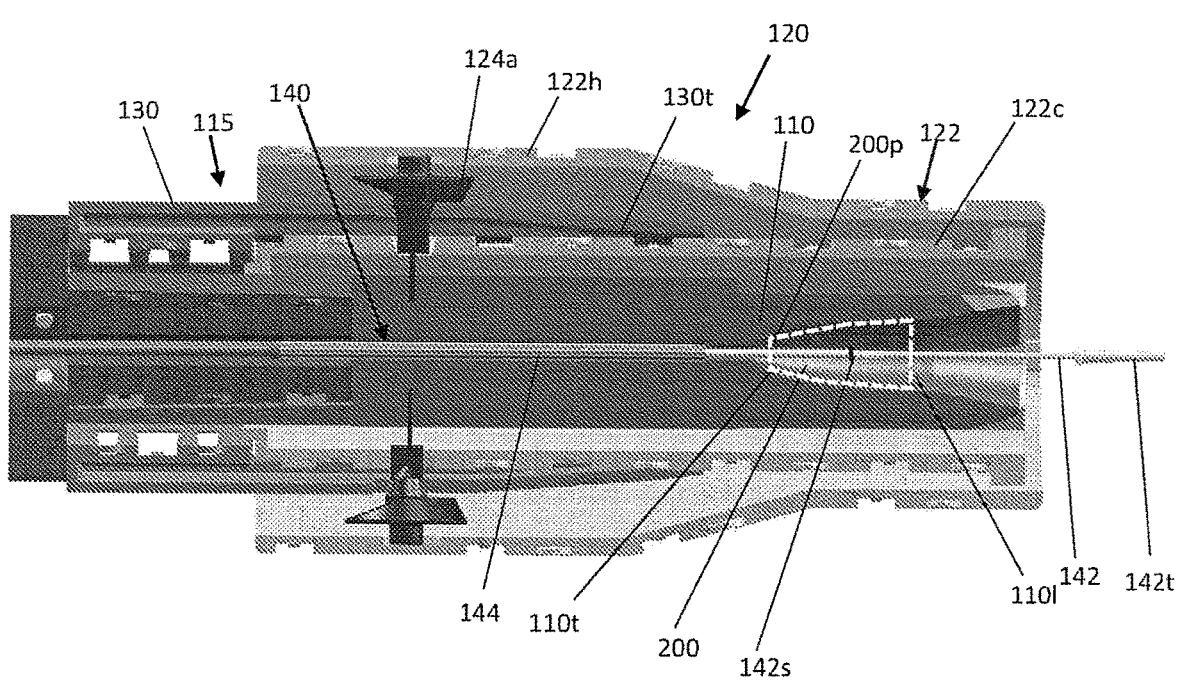

With reference to FIGS. 4A and 4B, once the loading pin shafts 124p have been removed from the longitudinal slots 110s of the tapered funnel structure 110 by the pin lift 130, the loading aid assembly 120 may undergo further longitudinal movement in a proximal direction relative to the funnel assembly 115. Because the inner luminal surface of the inner collar 122c of the loading aid assembly 120 is provided with a taper in the particular embodiment shown, such further longitudinal movement acts to close the pin slots 110s and reduces the inner diameter of the tapered funnel structure 110, including the inner diameter of the tapered region 110t of the loading lumen 110l therein, which further reduces the inner diameter of at least the proximal end 200p of the scaffold 200. A perspective view of the system at this point is provided in FIG. 10.

The inner member 142 may then be retracted relative to the outer sheath 144. During retraction, the scaffold lock 142s engages the proximal end of the scaffold 200p and draws the remainder of the scaffold 200 through the tapered region 110t of the loading lumen 110l and into the outer distal capsule 144d of the delivery catheter.

With reference now to FIG. 11, a delivery catheter handle 300 such as the Versatility™ universal handle available by Vention Medical Inc., South Plainfield, NJ, USA, may be used to translate the two coaxial shafts 142,144 of the catheter. The handle shown has two thumbwheels 302,304, which are attached to each of the shafts 142,144. A ball screw translates rotational motion to linear motion to move each of the shafts 142,144. Also shown is a flush port 312 for flushing the outer sheath 144 and a second flush port 314 for flushing the inner guidewire lumen of the inner member 142.

Once loaded, the outer sheath 144 constrains the scaffold (in the outer distal capsule 144d) for delivery and expansion into the vessel. The inner member 142 may provide a lumen by which the delivery catheter 140 tracks over a guidewire (not shown). The outer sheath 144 facilitates a fixed distance from the operator to the delivery site and the system allows for controlled movement of the inner 142 and outer 144 components to accurately deploy the scaffold 200. Once the delivery catheter 140 is tracked over a guidewire to the intended implant location, deployment may be achieved by rotating the proximal thumbwheel 302 which retracts the outer sheath 144, allowing the scaffold to expand into the intended body lumen. The scaffold lock feature 142s secures the scaffold's 200 proximal end 200p within the delivery catheter, such that recapture or repositioning is possible up to a certain point in deployment if the operator is not satisfied with the initial deployment location.

Although various embodiments are specifically illustrated and described herein, it will be appreciated that modifications and variations of the present disclosure are covered by the above teachings and are within the purview of the appended claims without departing from the spirit and intended scope of the disclosure.

The invention claimed is:

1. A method of scaffold delivery, comprising:
   (a) providing (1) a self-expanding scaffold and (2) a scaffold delivery system comprising (i) an elongate member, (ii) a tapered loading member comprising a loading lumen, (iii) at least one loading pin engaged with the scaffold, and (iv) a delivery sheath comprising a delivery lumen in communication with the loading lumen;
   (b) inserting said scaffold into said lumen;
   (c) moving said at least one loading pin longitudinally towards said delivery sheath such that said scaffold also moves longitudinally towards the delivery sheath, wherein the at least one loading pin extends through the scaffold and into the elongate inner member and the moving of said at least one loading pins also moves the elongate member towards the delivery lumen.

2. The method of claim 1, wherein the tapered loading member further comprises slots and the moving of said at least one loading pin in step (c) is done within said slots.

3. The method of claim 1, wherein said delivery system further comprises a loading pin engagement member.

4. The method of claim 3, further comprising the step of reversibly engaging said one or more loading pins with said loading pin engagement member prior to step (c).

5. The method of claim 4, wherein the loading pin engagement member is a ring-shaped member.

6. A delivery assembly comprising:
   (a) an elongate inner member;
   (b) a tapered loading member that comprises a loading lumen;
   (c) a self-expanding scaffold disposed around the elongate inner member within the loading lumen;
   (d) at least one loading pin configured for engagement with the scaffold and for movement through the loading lumen, wherein the at least one loading pin extends through the scaffold and into the elongate inner member and the moving of said at least one loading pins also moves the elongate inner member towards the delivery lumen; and
   (e) a delivery sheath comprising a delivery lumen in communication with the loading lumen.

7. The method of claim 6, wherein the tapered loading member further comprises slots and the movement of said at least one loading pin in step (d) is done within said slots.

8. The method of claim 6, wherein said delivery system further comprises a loading pin engagement member.

9. The method of claim 8, wherein the loading pin engagement member is a ring-shaped member.

* * * * *